United States Patent
Eastman et al.

(10) Patent No.: US 9,439,806 B2
(45) Date of Patent: Sep. 13, 2016

(54) FOOT PEDAL SYSTEM AND APPARATUS

(71) Applicant: Abbott Medical Optics Inc., Santa Ana, CA (US)

(72) Inventors: Brian J Eastman, Irvine, CA (US); Kelvin Kao, Long Beach, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 597 days.

(21) Appl. No.: 13/922,487

(22) Filed: Jun. 20, 2013

(65) Prior Publication Data

US 2014/0378986 A1 Dec. 25, 2014

(51) Int. Cl.
*A61F 9/007* (2006.01)
*A61B 17/00* (2006.01)

(52) U.S. Cl.
CPC .......... *A61F 9/00736* (2013.01); *A61B 17/00* (2013.01); *A61F 9/00745* (2013.01); *A61B 2017/00199* (2013.01); *A61B 2017/00212* (2013.01); *A61B 2017/00973* (2013.01); *A61B 2034/742* (2016.02); *A61B 2217/007* (2013.01)

(58) Field of Classification Search
CPC ..................... A61B 17/00; A61B 2017/00199; A61B 2017/00212; A61B 2019/2276; A61B 2019/2292; A61B 2217/007; A61B 2017/00973; A61F 9/00736; A61F 9/00745
USPC ............................................. 606/107; 73/490
See application file for complete search history.

(56) References Cited

U.S. PATENT DOCUMENTS

| | | | |
|---|---|---|---|
| 4,983,901 A | 1/1991 | Lehmer | |
| 5,524,180 A * | 6/1996 | Wang | A61B 19/22 600/117 |
| 6,086,598 A | 7/2000 | Appelbaum et al. | |
| 6,360,630 B2 | 3/2002 | Holtorf | |
| 6,452,120 B1 * | 9/2002 | Chen | G05G 1/30 200/52 R |
| 7,074,179 B2 * | 7/2006 | Wang | A61B 19/22 414/2 |
| 2001/0020401 A1 * | 9/2001 | Holtorf | G05G 1/30 74/560 |
| 2002/0070840 A1 | 6/2002 | Fischer et al. | |
| 2003/0004497 A1 * | 1/2003 | Chappuis | A61B 17/1626 606/1 |
| 2003/0047434 A1 * | 3/2003 | Hanson | A61B 17/00 200/86.5 |
| 2003/0051985 A1 * | 3/2003 | Chen | G05G 1/30 200/86.5 |
| 2003/0073980 A1 * | 4/2003 | Finlay | A61B 17/00 606/1 |
| 2010/0198200 A1 | 8/2010 | Horvath | |
| 2011/0092887 A1 * | 4/2011 | Wong | A61B 17/00 604/22 |
| 2011/0098721 A1 * | 4/2011 | Tran | H01H 21/26 606/130 |
| 2011/0248009 A1 | 10/2011 | Long et al. | |
| 2012/0083800 A1 * | 4/2012 | Andersohn | A61F 9/00736 606/130 |
| 2013/0169412 A1 * | 7/2013 | Roth | H01H 3/14 340/6.1 |

FOREIGN PATENT DOCUMENTS

WO  WO-2010054140 A2  5/2010

OTHER PUBLICATIONS

International Search Report and Written Opinion for Application No. PCT/US2014/043096, mailed on Sep. 17, 2014. 9 pages.

\* cited by examiner

*Primary Examiner* — Lisa Caputo
*Assistant Examiner* — Philip Cotey
(74) *Attorney, Agent, or Firm* — Abbott Medical Optics Inc.

(57) ABSTRACT

A phacoemulsification system and method, and a foot pedal device, system and method. The devices, systems and methods may include a console comprising a plurality of modes for at least one physically associated surgical instrument, and a foot pedal communicatively associated with said console and suitable for varying ones of the plurality of modes. The foot pedal may include a foot pedal base, and at least two electronically actuated sensors physically associated with the foot pedal base, communicatively connected to the console, and suitable for receiving physical indications of variations in ones of the plurality of modes.

20 Claims, 6 Drawing Sheets

FIG. 1

(PRIOR ART)

FOOT PEDAL SYSTEM AND APPARATUS

BACKGROUND OF THE DISCLOSURE

1. Field of the Disclosure

The present invention is generally related to methods, systems and apparatuses for controlling surgical aspects, particularly during treatment of an eye, and more particularly for controlling surgical aspects using a foot pedal.

2. Description of the Background

Ophthalmic surgical apparatuses, such as phacoemulsification apparatuses, typically include operating controls for regulating parameters or functions of the apparatuses. A phacoemulsification apparatus is particularly directed to the surgical removal of the natural, crystalline lenses from cataractic eyes, such as to allow for and/or prior to the insertion of an artificial intraocular lens.

Such an apparatus typically includes a control console, power supply, one or more pumps and associated electronic hardware (and, for the control console, software) for operating a multifunction surgical implement to ultrasonically emulsify eye tissue, irrigate the eye with a saline solution and aspirate the emulsified lens from the eye. Typically, such surgical implements are handheld.

In view of the handheld nature of the instrumentation necessary for a phacoemulsification procedure, it is generally desirable that the hands of a surgeon remain as free as possible during performance of a surgery. Accordingly, foot controls, such as in the form of a mechanical foot pedal, are frequently provided in order to facilitate use of the handpiece by delegating other control functions to the foot pedal device.

Any number of foot pedal device systems have been utilized, and those utilized include a variety of pneumatic and electrical actuators to control the ophthalmic surgical apparatus. For instance, improved foot pedal control systems such as those described in U.S. Pat. No. 4,983,901 provide for a great number of control variations and modes for operating phacoemulsification apparatus. One popular type of foot control is termed a dual-control foot pedal because of the two directions of foot movement available to actuate the controls. For example, in a dual-control pedal, a treadle (the actual pedal) may be pivoted in a vertical plane (pitch), as in a standard car accelerator-type pedal, while also being rotated in a horizontal plane, or yaw, direction. In addition to the dual treadle control, one or more other foot-actuated switches placed close to the treadle are often provided for easy access.

The foot pedal must be user friendly in order to provide a surgeon comfort and reliability in its use, so as not to initiate disruption of the surgeon's concentration when performing surgery. For example, during control of the foot pedal, the surgeon's posture is influenced by efforts to prevent losing contact with the foot pedal, which is typically achieved by keeping one foot flexed above the pedal and loading the body weight on the other foot. This causes a non-ergonomic posture which can lead to physical discomfort, and sometimes mistakes in control of the foot pedal.

Furthermore, as may be expected, different types of foot pedals are preferred by different surgeons, with some surgeons preferring an accelerator-type pedal in which the sole of the surgeon's foot is utilized for depression, while others desire a pedal engageable by the surgeon's toe in order to depress the pedal. This, of course, has led to the development of a multitude of foot pedal devices of diverse configurations in order to provide the comfort and reliability desired by individual surgeons. For instance, U.S. Pat. No. 6,360,630 to Holtorf discloses a dual position foot pedal rotatably mounted to a base in order to be operated by the toe or sole of a user's foot. However, even with such flexible designs, a change in foot pedals is often required when a phacoemulsification apparatus is utilized in sequence by different physicians, which is inconvenient and may require recalibration of the apparatus. In addition, such alternative foot pedals may not be available or even offered by a manufacturer.

Despite the availability of a number of relatively effective foot pedal designs employing the aforementioned mechanical actuation monitored by electrical encoders, potentiometers, and the like, there is a need for a surgical foot pedal that provides a decrease in mechanical failures and improved ergonomics. Such an apparatus and system would enhance a surgeon's comfort and concentration, and minimize moving mechanical components and interfaces.

SUMMARY OF THE INVENTION

The present invention provides at least a phacoemulsification system and method, and a foot pedal device, system and method.

The present invention may include a console comprising a plurality of modes for at least one physically associated surgical instrument, and a foot pedal communicatively associated with said console and suitable for varying ones of the plurality of modes. The foot pedal may include a foot pedal base, and at least two electronically actuated sensors physically associated with the foot pedal base, communicatively connected to the console, and suitable for receiving physical indications of variations in ones of the plurality of modes.

The present invention may additionally include a foot pedal suitable for use in a phacoemulsification system. The foot pedal may be communicatively associated with a console and suitable for varying ones of a plurality of phacoemulsification modes provided by the console, and may include a foot pedal base and at least two electronically actuated sensors physically associated with the foot pedal base, communicatively connected to the console, and suitable for receiving physical indications of variations in ones of the plurality of phacoemulsification modes.

Thus, the present invention provides at least a surgical foot pedal that provides a decrease in mechanical failures and improved ergonomics. The provided apparatus and system enhances a surgeon's comfort and concentration, and minimizes moving mechanical components and interfaces.

BRIEF DESCRIPTION OF THE DRAWINGS

The present invention is best understood with reference to the following detailed description of the invention and the drawings, in which like numerals refer to like elements, and in which.

DETAILED DESCRIPTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined herein.

Figure 1:
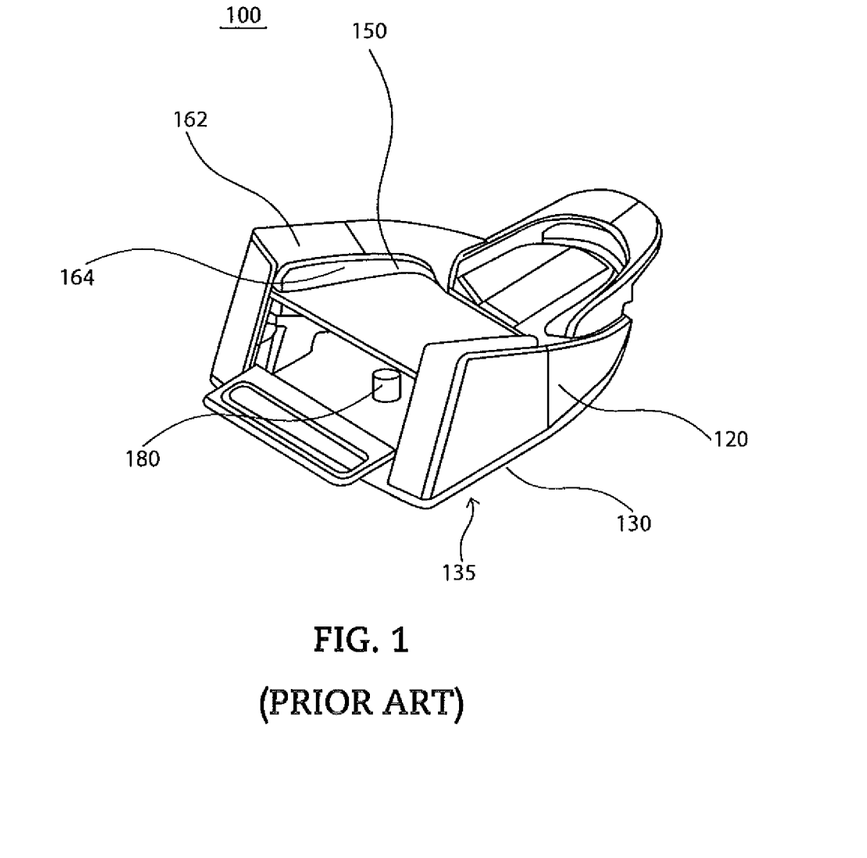
FIG. 1 illustrates a prospective view of a foot pedal control for use in a surgical system.

FIG. 1 is a prospective view of a typical mechanically-actuated foot pedal control 100 for use in a surgical system, such as for use during an ophthalmic surgery. The foot pedal controller 100 comprises a base 130 on which is mounted body housing 120 and a treadle 150. The base 130 may have an undercarriage 135 arranged to lie flat on a ground surface. The base may provide improved stability in undercarriage embodiments based on inclusion of a gripping surface, such as rubber, rubberized, plastic, or like traction strips or treads (not shown).

For purposes of orientation, the foot pedal controller 100 extends upward from the base 130, a forward or anterior direction is defined as to the left in FIG. 1, and a rearward or posterior direction is defined as to the right. The various components of the foot pedal controller 100 may be made from any suitable material or combination of materials, such as stainless steel, titanium, or plastic.

Top switch assemblies 162 may be suitably and actuatably mounted on the body housing 120. In embodiments, side switches 164 may be suitably and actuatably mounted to, and/or otherwise associated with, housing 120 or treadle 150. Movement of treadle 150 may typically be assessed based on pressure/depressure on a potentiometer or on suitable pneumatics, that is, based on actuation of mechanical or electromechanical elements. Likewise, actuation of top switches 162 and side switches 164 is generally, at least in part, mechanical and/or electromechanical.

For example, pressure exerted on treadle 150 may cause a rotation about an axis of the treadle 150, and may thereby cause the rotation/depression of a potentiometer physically associated with a portion of the underside of treadle 150. This depression of the potentiometer generates an electrical signal correspondent to the resistance change in the potentiometer, which resistance change is itself correspondent to the distance traveled by the treadle 150. The signal generated by the potentiometer may then be received by the surgical console, and may allow a program running on the console to determine the position of the treadle 150. In this way, the user may control different surgical modes and/or functionality provided through the surgical console.

However, in such embodiments, mechanical actuation monitored by electrical encoders, potentiometers, and/or the like provides numerous critical system points that may suffer mechanical or electromechanical failure. Moreover, the structure illustrated in the example of FIG. 1 and necessitated by these multiple points of mechanical actuation may be ergonomically inconvenient for a surgeon. For example, a foot pedal controller 100 such as that of FIG. 1 may cause the surgeon to have to affirmatively suspend her foot if it is not desired that the treadle be actuated. This may not only be uncomfortable for the surgeon, but may additionally distract the surgeon's attention.

Accordingly, the present disclosure provides exemplary embodiments that may remove some or all mechanical and electromechanical components, thereby significantly reducing the potential for mechanical failures of aspects of the foot pedal controller. The elimination of mechanical components may be accomplished, at least in part, by detecting the position of a surgeon's foot position using electrical sensors and/or sensor arrays, such as infrared sensors, optical sensors, wave emitting transmitter/receiver sensors, imaging devices (such as cameras), and arrays and/or combinations thereof. The sensors/sensor arrays may be located under, in front of, behind, on top of, alongside, or on the surgeon's foot in order to detect the linear and/or angular travel of the foot, such as along a vertical and/or horizontal axis with respect to the floor.

By way of non-limiting example, sensors may detect: the front of the foot (toes) being raised or lowered; the back of the foot (heel) being raised or lowered; the front of the foot (toes) translating/rotating left or right; and/or the back of the foot (heel) translating/rotating left or right. More particularly, sensors may surround, be suspended about and/or be arrayed adjacent to the foot as the foot rests on the floor, sensors may surround and/or be placed or arrayed underneath the foot in a footpedal and/or thin "foot mat" that may support the foot, or the sensors may be mounted in a device that the user wears on the foot.

Figure 2A:
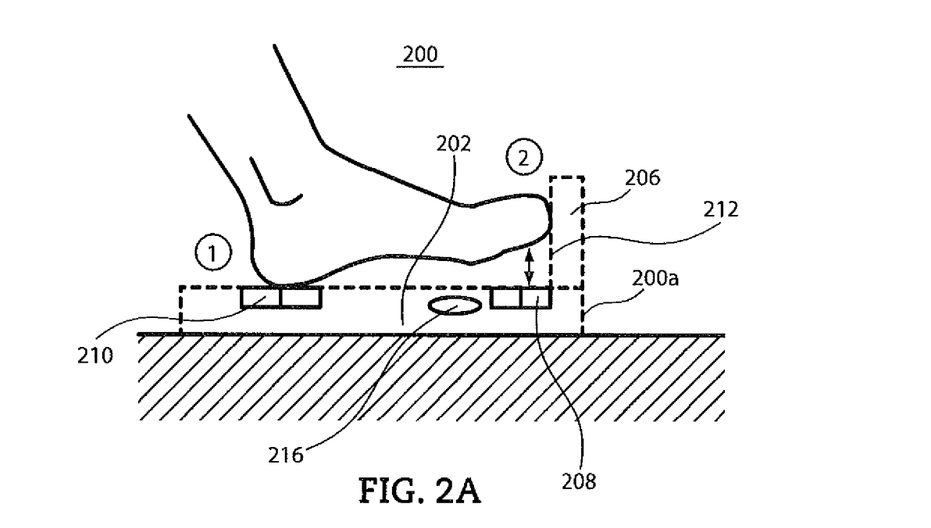
FIGS. 2A and 2B illustrate side views of an exemplary foot pedal controller.
Figure 2B:
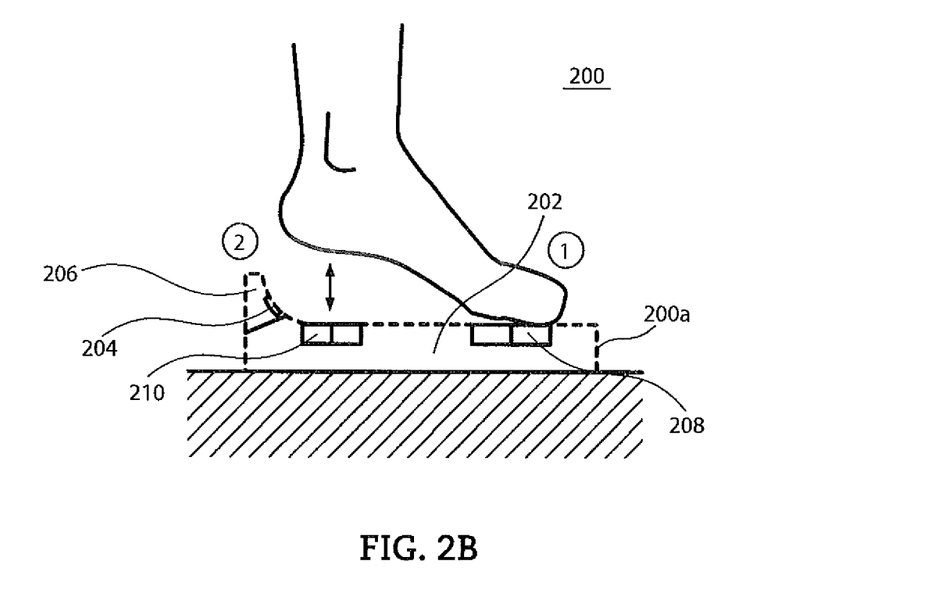

FIGS. 2A and 2B are side views illustrating an exemplary foot pedal controller 200. The illustrated foot pedal controller is a non-mechanically actuated, herein defined to be substantially or completely electrically/electronically actuated, foot pedal controller 200. The particular electrically actuated foot pedal illustrated in the example of FIG. 2 is a base plate style foot pedal 200a comprising a base plate 202.

The electrically actuated foot pedal 200 may, in certain exemplary embodiments, include one or more safety switches 204, such as to detect that a foot is in the proper position prior to allowing actuation of a surgical console (not shown) based on movement of the foot. For example, safety switch 204 may comprise a proximity sensor, such as an infrared sensor, placed at the back of the foot pedal 200 to detect the presence of a heel to confirm that it is planted and ready for surgery (of course, safety switch 204 may likewise be provided to detect the presence of toes, heel and toes, instep, a foot of particular size, or the like, in alternative and additional embodiments). Thereby, the foot pedal 200 may allow for actuation of surgical aspects only when a heel is placed and sensed in the designated location. Accordingly, false or inadvertent reads may be avoided, such as might otherwise occur when the surgeon is initially placing her foot.

The safety switch 204 may be executed in software, hardware, or a combination thereof. For example, software may only read a "toe switch" (i.e., a switch at the anterior portion of the foot pedal 200) after the heel is detected as planted in the proper position proximate to safety switch 204, and the software may additionally not read the toe switch until a predetermined safety time for foot adjustment has passed. The predetermined safety time may be from one to three seconds, preferably one to two seconds. In an embodiment, the user may set the predetermined safety time to her preference via the GUI.

In embodiments, the foot pedal 200 may also include a toe and/or heel stop/rest 206, such as integrated with, or distinct from, the remaining portions of foot pedal 200. Such a stop/rest 206 may also be adjustable, such as to accommodate different size feet, may be utilized to increase comfort and improve ergonomics, and may ensure that the surgeon has positioned her foot in the proper foot location. A stop/rest may further ensure the consistent placement and positioning of a foot with respect to some or all of the sensors of the foot pedal 200. Each stop/rest 206 may be integral with the remainder of the foot pedal 200, or may be physically distinct from other aspects of the foot pedal 200.

If so required, once the foot pedal, or, in some embodiments, the console software system reading the foot pedal output signals, has determined that the foot is in place, the sensor(s) 208, 210 indicating the position of the foot within the foot pedal 200 may be read. In the exemplary base plate embodiment of FIGS. 2A and 2B, when the foot is resting on the base plate, the location may be computed, based on the indication from the sensor(s) 208, 210, as 0% travel, for example, and when the front of the foot is raised one inch, the location/distance may be computed by the sensor(s) as 50% travel, for example, and when the front of the foot is raised two inches, the location/distance may be computed by the sensors as 100% travel, for example.

In certain embodiments, any distance the foot travels over 100% travel may be calculated as 100% travel. Thus, in above example, if the foot is raised 2.2 inches, the indication would be 100% travel. In alternative embodiments, the system may ask if the user wishes to recalibrate, such as when a particular number of over 100% motions are performed, such as in quick succession. Moreover, in embodiments, travel of a certain type or extent, such as over 100%, may indicate additional functionality, such as indicating a "scroll mode(s)" feature to the GUI on the console.

Further, in the foregoing example, once the foot is placed back at the flat position, i.e., at rest, the system may read 0% travel, and may wait for the user to raise her foot again. Alternatively, the user may simply raise her foot to the desired level, and subsequently place the foot at rest, without the system indicating a 0% travel location once the foot is at rest. Thereby, the user need not maintain her foot at a travelled position, but rather can rest the foot immediately after giving an indication. In such embodiments, a second "tap" at the 0% position may be required in order to indicate a return to the 0% travel position. In exemplary embodiments, if the safety sensor 204 senses that the heel is no longer in position, 0% travel may be assumed until a confirmed foot placement is once again established.

Travel distances may be assessed by sensors 208 and 210 independently, or in conjunction, or both. For example, sensor 208 may indicate the travel distance of the user's toe, either rotationally/horizontally or vertically, and sensor 208 may or may not be sensed independently solely during blocking or substantial blocking of sensor 210 (i.e., during presence or near proximity of a heel on sensor 210). Sensor 210 may indicate the travel distance of the user's heel, either rotationally/horizontally or vertically, and sensor 210 may or may not be sensed independently solely during blocking or substantial blocking of sensor 208 (i.e., during presence or near proximity of toes on sensor 210). Sensors 208 and 210, in conjunction, may indicate travel distance of the entire foot, i.e., of the heel and the toe.

As referenced above, because the distance that each surgeon can comfortably lift or rotate her foot may be a unique distance, each surgeon's settings may need to be established for particular travel distances, and/or the correspondences between particular travel and surgical aspects. This calibration and correspondence will be, of course, performed in association with the software resident on the surgical console. For example, a surgeon may set her foot on the foot pedal 200, and may raise her toes a certain distance, and may indicate at the console that this distance is to be stored in her unique profile as a 100% travel height. That is, the user may perform movements responsive to indications from the console or foot pedal 200, or may enter indications to the console, such as by pressing a "read" or "calibrate" button, to perform calibration consistent with the user's movements.

Accordingly, the console system may store a series of unique profiles, including, for example, maximum travel distances, correspondences to surgical aspects, and the like under each surgeon's settings. By way of non-limiting example, the console may provide this feature as a utility that allows for the prompting of the surgeon to comfortably lift her foot (or repeatedly lift her foot or parts thereof), and the system may correspondingly set those movements, as sensed by the sensors 208, 210, as the value of certain travel distances and correspondences for that surgeon. Similarly, distances that indicate surgical aspects, as used herein, may be defined to include speed of movement, types of movement (i.e., linear versus circular), series of movements, or the like, and the calibrations/correspondences may be indicated by combinations or averages thereof.

In another embodiment, the surgeon may set the distance/control regions between 0% and 100% travel. For example, 0% to 30% may be set for controlling irrigation in a linear or panel manner, 31% to 60% may be set for controlling irrigation and aspiration in a linear or panel manner, and 61% to 100% maybe set for controlling irrigation, aspiration, and ultrasonic power in a liner or panel manner based on the angle and/or range suitable to the surgeon.

The foot pedal 200 may provide feedback or like indications to the surgeon when actuations occur, i.e., when predetermined travel distances to indicate modifications to surgical aspects are reached. For example, the foot pedal 200 may enclose or otherwise provide a feedback device 212, such as in the form of tactile feedback (i.e., solenoids, such as a solenoid hammer; piezoelectrics, such as a vibrator; motors, such as an off-center cam motor) indicating travel distance levels, and/or audible feedback, such as tone pitch or buzzer, provided by the console or the foot pedal 200. For example, an ultrasonic pitch feedback may increase as power is increased in a particular mode, or may vary for irrigation activation, aspiration activation, and vitrectomy cutting speed.

Moreover, and as discussed above with respect to FIG. 1, current foot pedals typically provide a number of mechanically actuated buttons/switches that are used for indicating a desire to vary additional surgical aspects. With respect to the instant disclosure, such buttons/switches may be in the form of additional proximity/infrared/optical sensors 216, such as may be located on the foot pedal 200, such as in a location discrete from sensors 208, 210, such as on bracing or rises physically associated with the foot pedal 200, or on bracing or rises physically disassociated with the foot pedal 200. Of course, actuation of sensors 216 may have particular requirements for actuation, such as were discussed with respect to other sensors herein, such as a predetermined time actuating a sensor 216 prior to deeming the presence of a foot as an intentional actuation. It may be preferable that the electronically actuated sensors discussed herein have similar sensitivity to the mechanically actuated sensors in a known foot pedal embodiment, such as that shown in FIG. 1.

More particularly, the electronically actuated foot pedal may house sensors 208, 210, 216 in any number and in any of many different locations, in order to read a variety of foot movements. For example, if sensors are to read the positional height of the toes, the sensors may be placed under the foot, as in sensors 208, on either side of the foot at the anterior of the foot pedal 200, at the front of the foot pedal 200, or above the toe position (forming, in essence, a front "boot" portion into which the foot may be inserted). Likewise, the sensor(s) may be affixed directly to the user's foot, such as in the form of a shoe, sock, or harness, by way of non-limiting example. As such, the disclosed foot pedal may be operable in conjunction with socked, bare, shoed, and covered shoes, by way of non-limiting example.

As such, the placement of sensors 208, 210, 216 in FIGS. 2A and 2B is illustrative only, and those skilled in the pertinent arts will appreciate, in light of the disclosure, that sensors may additionally or alternatively be placed in many locations other than those illustrated in FIGS. 2A and 2B. Correspondingly, sensors 208, 210, 216 may be singular sensors, paired sensors, or sensor arrays, although overuse of sensor arrays may add unwanted expense to the production of a foot pedal 200 according to the disclosure.

Yet further, it will be appreciated that although electronically actuated sensors are deemed preferred for use in the instant disclosure, such sensors may be combined with/ partially replaced by mechanically actuated sensors and/or mechanical aspects in certain embodiments and still achieve many of the advantages and benefits discussed herein. For example, the foot pedal 200 may include a partial or complete treadle, such as may be rotated about a pin through two side braces. Moreover, the partial treadle may be sized so as to only cover the instep of the user, thereby leaving the heel and toes of the user to actuate the electronic sensors 208, 210, 216 discussed herein. Further, a partial treadle may be sized so as to be in contact with only the heel, or only the toe(s), of the user. Moreover, a partial treadle may be provided as a foot rest or pivot point, rather than as an actuator for sensors 208, 210, 216. It will be appreciated that such a treadle may have associated therewith one or more springs, such as to provide back pressure on the user's foot and a return to position of aspects of the treadle.

Moreover, one or more of the sensors 208, 210, 216, and hence the foot pedal 200, may be bi-lateral in nature, at least in that, if the foot pedal 200 is rotated by the user, sensor 208 may read the heel travel, rather than the toe travel in the illustration of FIGS. 2A and 2B, by way of non-limiting example. Further, the switches 208, 210, 216 may be adjustable, such as may allow for the aforementioned bi-lateral nature of the foregoing exemplary foot pedal.

Figure 3:
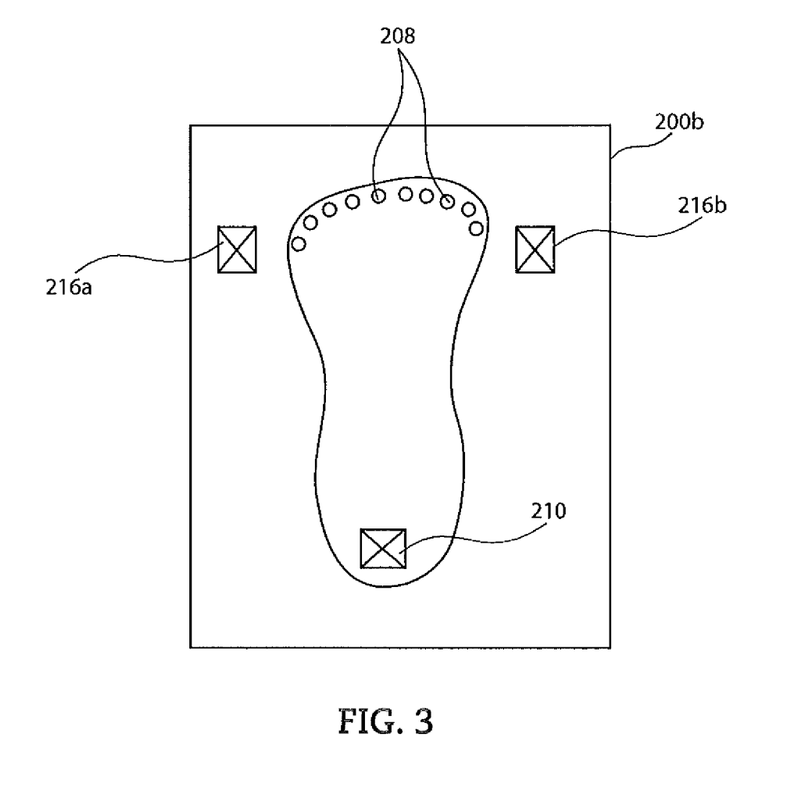
FIG. 3 is a top view illustrating an exemplary foot pedal controller.

FIG. 3 is a top view illustrating an exemplary foot pedal having electronically actuated sensors 208, 210. In the illustrated embodiment, foot pedal 200b comprises a "mat" style foot pedal. In the illustration, the toe sensors 208 comprise a sensor array that senses the raising and rotation of the toes, and the heel sensor 210 comprises a single sensor. Further illustrated on the mat are left and right additional sensors 216a, 216b, which are suitable for providing the functionality provided by the top switches shown in FIG. 1. Of course, those skilled in the art will appreciate that other sensors, such as discussed above with respect to FIGS. 2A and 2B, may be provided in association with mat foot pedal 200b, such as in association with rises or braces proximate to the mat foot pedal 200b. Likewise, the mat foot pedal may include stops/rests and/or one or more safety switches.

Mat foot pedal 200b may be of any suitable material for containing therein at least sensors 208, 210, for protecting said sensors, for allowing said sensors to "see" through any protective/waterproof material associated with mat foot pedal 200b, and for enclosing any wiring and the like. Further, in certain embodiments the mat foot pedal 200b may be foldable or rollable, such as to allow for easy movement or transport. Thus, mat foot pedal 200b may have multiple layers, such as having opaque layers to enclose certain wiring and electronics, and at least one clear protective layer covering the opaque layers to allow the sensors to "see" through the protective layer. Such layers may be formed of any suitable composition for use in a sterile environment, such as, but not limited to, plastics, vinyls, PVC, and the like.

Figure 4A:
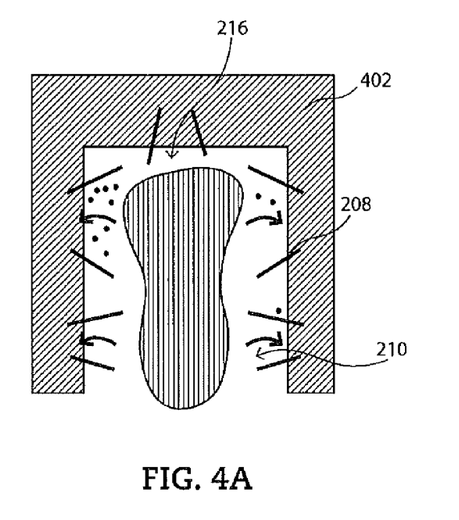
FIGS. 4A and 4B are views illustrating an exemplary foot pedal controller.
Figure 4B:
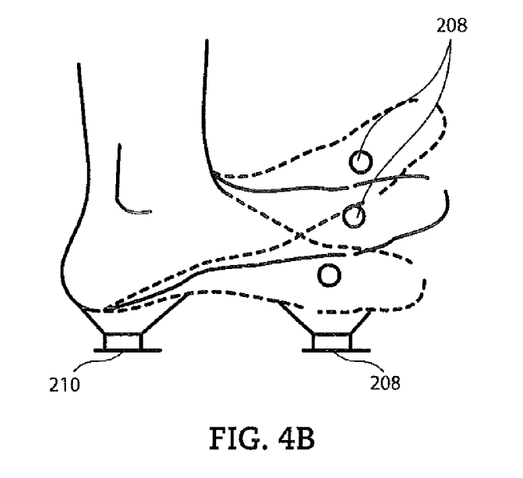

FIGS. 4A and 4B are top and side views, respectively, illustrating an exemplary foot pedal having electronically actuated sensors 208, 210. In the illustrated embodiment, foot pedal 200c comprises a frame style foot pedal having a frame 402 that surrounds a user's foot. In the illustration, the toe sensors 208 may comprise one or more side wall, side facing sensors (or a side facing sensor array) that sense the raising and rotation of the toes. Additionally, a base plate 202 or mat style pedal 200b as shown in FIGS. 2A, 2B, and 3 may be provided in conjunction with frame 402, and accordingly there may be provided upward facing toe sensors 208 as discussed elsewhere herein. Similarly, the heel sensor 210 may be provided and may comprise a single, upward facing sensor 210, or side facing sensors 210. Other sensors may optionally include, for example, front sensors 216. Of course, those skilled in the art will appreciate that other sensors, such as those discussed above with respect to FIGS. 2A and 2B, may be provided in association with frame foot pedal 200c, such as in association with rises or braces proximate to the frame foot pedal 200c. Likewise, the frame foot pedal may include stops/rests and/or one or more safety switches.

Figure 5A:
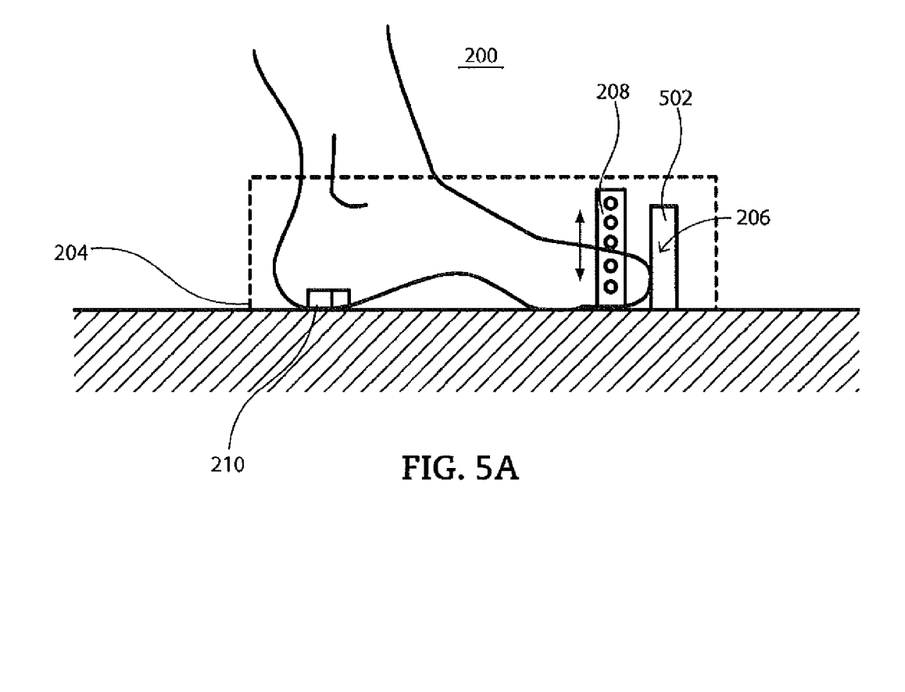
FIGS. 5A and 5B is a side view illustrating an exemplary foot pedal controller.
Figure 5B:
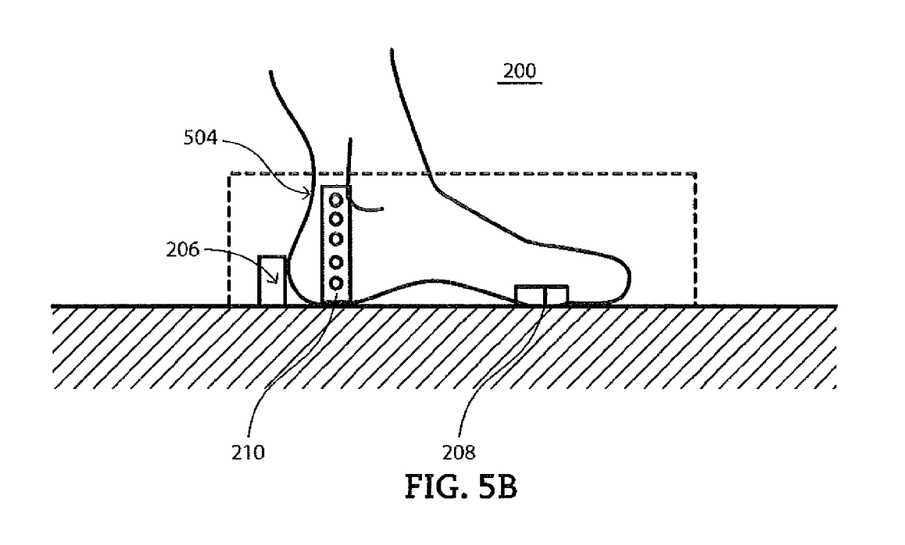

FIGS. 5A and 5B illustrate additional exemplary aspects of a foot pedal 200 having electrically actuated sensors. FIG. 5A illustrates an exemplary embodiment wherein toe sensors 208 are provided as an array on a brace 502. FIG. 5B illustrates an exemplary embodiment wherein heel sensors 210 are provided as an array on brace 504. Also illustrated are toe sensors 208 and heel sensors 210, which may be provided in conjunction with heel brace 504 and toe brace 502, respectively, such as in embodiments additionally including a mat style or base plate style foot pedal as shown in FIGS. 2A, 2B, and 3. Of course, other combinations, such as embodiments having heel brace 504 and toe brace 502 simultaneously, with or without either or both of toe sensor 208 and heel sensor 210, may be provided according to the disclosure. Further provided may be rests/stops 206, which may include, for example, one or more safety switches 204. Alternatively, sensor 208, 210 may provide the functionality of safety switch 204. Additionally, this and other embodiments may include a foot enclosure (not shown), such as may surround all or a portion of a user's foot, and which may include the enumerated and other sensors 208, 210, 216, switches 204, and/or rests/stops 206.

The foot pedal controller 200 may be powered by a battery source and may include a rechargeable battery. As may be appreciated by those skilled in the art, a charging station may be used to recharge a rechargeable battery and may be incorporated in the associated console, for example. Similarly, if the foot pedal controller 200 is hard wired to the console, such a linkage may supply any necessary power. As with the foot pedal controller 200 as a whole, any battery and/or battery compartment may be sufficiently sealed to provide a waterproof system.

Figure 6:
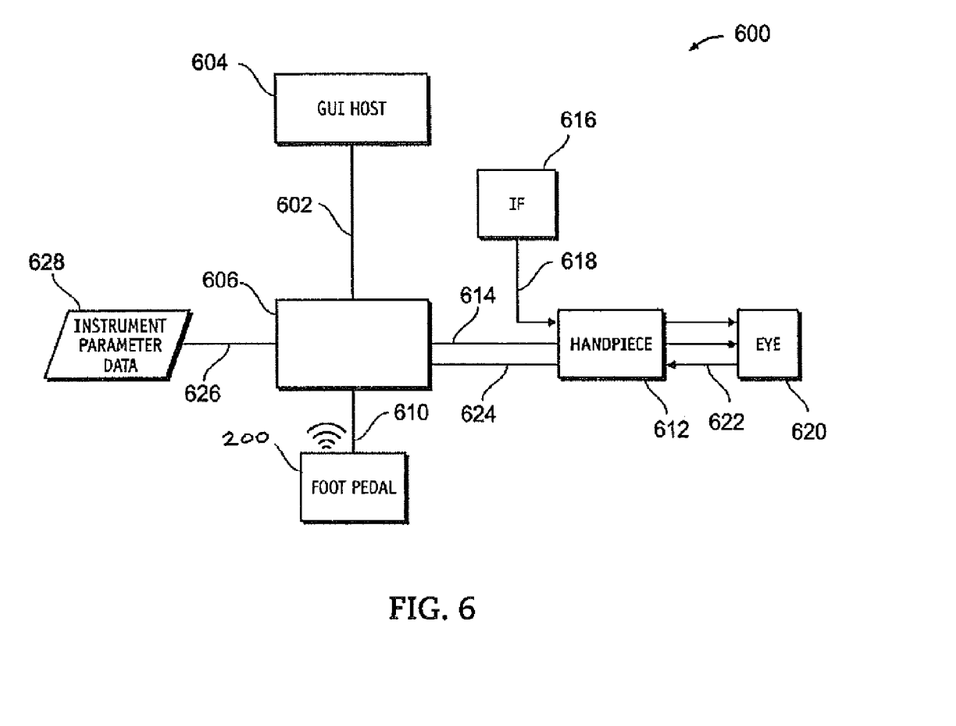
FIG. 6 is a schematic of an exemplary system in which a foot pedal control may operate.

As discussed above and as illustrated with respect to the exemplary embodiment of FIG. 6, each travel position reached through actuation of the foot pedal 200 by, for example, a user's foot, may be visually indicated on at least one graphical user interface (GUI) 604 of the console system 600 communicatively associated with the foot pedal 200. As such, the programmable travel positions of the foot pedal 200 may control different functions provided by the console 606 and/or may be additive in nature. For example, a first travel position for foot pedal 200 may be programmed to have the console 606 provide an irrigation function, a second position may add an aspiration and irrigation function, and a third position may add an ultrasound function to the aspiration and irrigation function. In addition, as discussed herein, other switches 216 may allow for control of the functions activated via the foot pedal 200. For example, if an aspiration function is activated, at least one other switch 216 may be programmed to control the strength of the vacuum applied. Similarly, at least one other switch 216 may control which function is otherwise controlled by switches 208, 210. Additionally, another switch 216 may be programmed to toggle through preprogrammed surgical modes or submodes indicated at the GUI of console system 600.

Although the present foot pedal control may be used in various environments and applications, a particularly useful application is in an ocular surgical system such as a phacoemulsification/vitrectomy system. An exemplary phacoemulsification/vitrectomy console system 600 for use in such an application is illustrated in the functional block diagram of FIG. 6. More particularly, FIG. 6 shows selected ones of the components and interfaces that may be employed in a safety-critical medical instrument system in which the foot pedal controller disclosed herein may be utilized.

A serial communication cable 602 may connect a GUI 604 and console 606 for the purposes of controlling the console 606 by the GUI host 604. The console 606 may be considered a computational device in the arrangement shown, but other arrangements are possible. A switch module associated with an exemplary foot pedal 200, such as described herein, transmits control signals relating internal physical and virtual switch position information as input to the console 606 over a serial communications cable 610, or wirelessly if desired. Console 606 may provide a database file system for storing configuration parameter values, programs, and other data saved in a storage device (not shown). In addition, the database file system may be realized on the GUI host 604, console 606, or any other subsystem (not shown) that could accommodate such a file system.

The system 600 has a handpiece 612 that typically includes a needle and electrical means, such as a piezoelectric crystal, for ultrasonically vibrating the needle. The console 606 supplies power on line 614 to the operative tip 612. An irrigation fluid source 616 can be fluidly coupled to operative tip 612 through line 618. The irrigation fluid and ultrasonic power are applied by the operative tip 612 to an eye 620, or other affected area or region. Alternatively, the irrigation source may be routed to the eye 620 through a separate pathway independent of the handpiece. Aspiration is provided from the eye 620 by one or more pumps (not shown), such as a peristaltic pump and/or venturi pump, via the console 606, through lines 622 and 624. A surgeon/operator may select an amplitude of electrical pulses either using the handpiece, via the instrument host and GUI host, using the foot pedal, and/or voice command.

An interface communications cable 626 connects to the console 606 for distributing instrument sensor/parameter data 628, and may include distribution of instrument settings and parameter information, to other systems, subsystems and modules within and external to console 606. Although shown connected to the console 606, interface communications cable 626 may be connected or realized on any other subsystem (not shown) that could accommodate such an interface device able to distribute the respective data.

While the invention has been described in its preferred embodiments, it is to be understood that the words which have been used are words of description and not of limitation. For example, the present disclosure may be applicable, in addition to surgical foot pedals, to other types of pedals, such as driving pedals, gaming pedals, and equipment operating pedals. Therefore, changes may be made to and within the appended claims without departing from the true scope of the invention.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

What is claimed is:

1. A foot pedal, comprising:
    a foot pedal base communicatively associated with a console and suitable for varying ones of a plurality of operating modes provided by the console;
    at least two electronically actuated sensors physically associated with the foot pedal base, communicatively connected to the console, and suitable for receiving physical indications of variations in ones of the plurality of operating modes; and
    at least one safety switch suitable to detect the presence of a foot in a proper position prior to allowing actuation of a surgical console based on movement of the foot.

2. The foot pedal of claim 1, further comprising at least one mechanically actuated sensor physically associated with the foot pedal base, communicatively connected to the console, and suitable for receiving the physical indications of variations in ones of the plurality of operating modes.

3. The foot pedal claim 1, further comprising a treadle associated with the foot pedal base, and wherein at least one of the electronically actuated sensors is physically associated with the treadle.

4. The foot pedal of claim 1, wherein at least one of the electronically actuated sensors comprises a sensor array.

5. The foot pedal of claim 1, wherein the electronically actuated sensors comprise ones selected from the group consisting of infrared sensors, optical sensors, wave emitting transceiver sensors, imaging devices, and combinations thereof.

6. The foot pedal of claim 1, wherein the electronically actuated sensors are located at least one selected from the group consisting of under, in front of, behind, on top of, alongside, and on the physical indication of the variations.

7. The foot pedal of claim 1, wherein the physical indication comprises at least one selected from the group consisting of toes being raised or lowered, heel being raised or lowered, toes translating left or right, and heel translating left or right.

8. The foot pedal of claim 1, wherein the at least one safety switch comprises a proximity sensor.

9. The foot pedal of claim 1, further comprising at least one foot stop.

10. The foot pedal of claim 9, wherein the at least one foot stop is integral with the foot pedal base.

11. The foot pedal of claim 1, wherein the physical indication comprises a distance travelled.

12. The foot pedal of claim 11, wherein the distance travelled comprises at least one selected from the group consisting of speed of movement, type of movement, series of movements, combinations thereof, and averages thereof.

13. The foot pedal of claim 1, wherein the console comprises a calibration mode variable by the physical indication.

14. The foot pedal of claim 13, wherein the calibration mode comprises a surgeon's profile.

15. The foot pedal of claim 1, further comprising a feedback device suitable for providing feedback of the physical indication.

16. The foot pedal of claim 15, the feedback comprising one of tactile feedback and audible feedback.

17. The foot pedal of claim 1, the foot pedal base comprising a foot mat.

18. The foot pedal of claim 1, the foot pedal base comprising a frame.

19. A phacoemulsification system, comprising:
   a console suitable for providing a plurality of operating modes for at least one surgical instrument connected to said console; and
   a foot pedal communicatively associated with said console and suitable for varying ones of the plurality of operating modes, comprising:
      a foot pedal base;
      at least two electronically actuated sensors physically associated with the foot pedal base and suitable for receiving physical indications directing variations in ones of the plurality of operating modes; and
      at least one safety switch suitable to detect the presence of a foot in a proper position prior to allowing actuation of a surgical console based on movement of the foot.

20. The foot pedal of claim 8, wherein the at least one safety switch detects the presence of a heel of the foot planted in a proper position proximate to the at least one safety switch.

\* \* \* \* \*